US00PP13424P2

(12) United States Plant Patent
Roberson

(10) Patent No.: US PP13,424 P2
(45) Date of Patent: Dec. 31, 2002

(54) LANTANA PLANT NAMED 'ROBPATPAS'

(76) Inventor: Robert J. Roberson, P.O. Box 210, Grain Valley, MO (US) 64029

( * ) Notice: Subject to any disclaimer, the term of this patent is extended or adjusted under 35 U.S.C. 154(b) by 0 days.

(21) Appl. No.: 09/895,635

(22) Filed: Jun. 30, 2001

(51) Int. Cl.[7] ..... A01H 5/00

(52) U.S. Cl. ..... Plt./227
(58) Field of Search ..... Plt./227

*Primary Examiner*—Kent L. Bell

(57) ABSTRACT

A distinct cultivar of Lantana plant named 'Robpatpas', characterized by its upright and outwardly spreading plant habit; mounded plant form; vigorous growth habit; rapid growth rate; freely flowering habit; and pale yellow to bright pink-colored flowers.

2 Drawing Sheets

BOTANICAL CLASSIFICATION/CULTIVAR DESIGNATION

*Lantana camara* cultivar 'Robpatpas'.

BACKGROUND OF THE INVENTION

The present Invention relates to a new and distinct cultivar of Lantana plant, botanically known as *Lantana camara*, and hereinafter referred to by the cultivar name 'Robpatpas'.

The new Lantana is a product of a planned breeding program conducted by the Inventor in Grain Valley, Mo. The objective of the breeding program is to create freely-flowering Lantanas with bright pink-colored flowers.

The new Lantana originated from a cross made by the Inventor during the spring, 1995, of the Lantana cultivar 'Robpathot', disclosed in U.S. Plant Pat. No. 12,266, as the female, or seed parent, with an unidentified Lantana selection as the male, or pollen parent. The new Lantana was selected during the winter, 1995, as a single plant from the resulting progeny by the Inventor in a controlled environment in Grain Valley, Mo., on the basis of its bright pink-colored flowers.

Asexual reproduction of the new cultivar by terminal cuttings taken in a controlled environment in Grain Valley, Mo., has shown that the unique features of this new Lantana are stable and reproduced true to type in successive generations.

SUMMARY OF THE INVENTION

Plants of the cultivar 'Robpatpas' have not been observed under all possible environmental conditionas. The phenotype may vary somewhat with variations in environment and culture such as temperature, light intensity, daylength, water status, and/or fertilizer rate or type without, however, any variance in genotype.

The following traits have been repeatedly observed and are determined to be the unique characteristics of 'Robpatpas'. These characteristics in combination distinguish 'Robpatpas' as a new and distinct Lantana cultivar:

1. Upright and outwardly spreading plant habit; mounded plant form.
2. Vigorous growth habit; rapid growth rate.
3. Freely flowering habit.
4. Pale yellow to bright pink-colored flowers.

Plants of the new Lantana are comparable to plants of the female parent, the cultivar 'Robpathot'. In side-by-side comparisons conducted in Grain Valley, Mo., plants of the new Lantana have bright pink-colored opened flowers whereas plants of the cultivar 'Robpathot' have magenta-colored opened flowers.

Plants of the new Lantana differ from plants of the male parent, the unidentified Lantana selection, and other Lantana cultivars known to the Inventor primarily in the new Lantana's unique combination of mounded plant habit, bright pink opened flower color, and freely-flowering habit.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph on the first sheet comprises a side perspective view of typical flowering plants of 'Robpatpas' grown in a hanging basket container.

The photograph on the second sheet comprises a close-up view of typical inflorescences and leaves of 'Robpatpas'.

DETAILED BOTANICAL DESCRIPTION

In the following description, color references are made to The Royal Horticultural Society Colour Chart except where general terms of ordinary dictionary significance are used. Plants used for the photographs and description were planted in hanging basket containers after rooting and grown for about 3 months during the spring in a polyethylene-covered greenhouse in Grain Valley, Mo. During the production of the plants, day temperatures were about 24° C. and night temperatures were about 18° C.

Parentage:

*Female parent.*—*Lantana camara* cultivar 'Robpathot', disclosed in U.S. Plant Pat. No. 12,266.

*Male parent.*—Unidentified *Lantana camara* selection, not patented.

Propagation:

*Type cutting.*—Terminal cuttings.

*Time to initiate roots, summer.*—About 13 days at 27° C.

*Time to initiate roots, winter.*—About 15 days at 27° C.

*Time to develop roots, summer.*—About 39 days at 29° C.

*Time to develop roots, winter.*—About 46 days at 24° C.

*Root description.*—Fine, fibrous; initially glaucous white in color then becoming tan, 161D, with development.

*Rooting habit.*—Freely branching.

Plant description:

*Form.*—Flowering subshrub; upright and outwardly spreading; mounded plant form. Freely branching; two lateral branches potentially forming at every node; pinching enhances lateral branch development.

*Plant height.*—About 22 cm.

*Plant diameter.*—About 48 cm.

*Vigor.*—Vigorous, rapid growth rate.

*Lateral branches.*—Length: About 18 cm. Diameter: About 3.5 mm. Internode length: About 4.2 cm. Strength: Flexible, but strong. Texture: Rough, pubescent. Color: Young: 144A. Woody: Closest to 165B.

*Foliage description.*—Leaves simple, generally symmetrical and long-persisting; opposite. Length: About 4.9 cm. Width: About 3.3 cm. Shape: Ovate. Apex: Acute. Base: Obtuse to truncate. Margin: Crenate to serrate with ciliation. Texture, both surfaces: Leathery, rough, coarse; slightly pubescent. Luster: Upper surface: Somewhat glossy. Lower surface: Dull. Venation pattern: Arcuate. Fragrance: Mint-like. Color: Young foliage, upper surface: More green than 146A. Young foliage, lower surface: More green than 146B. Mature foliage, upper surface: More green than 146A. Mature foliage, lower surface: More green than 147B. Venation, upper surface: 146A. Venation, lower surface: Close to 147C. Petiole length: About 8 mm. Petiole diameter: About 1.5 mm. Petiole texture, both surfaces: Slightly pubescent. Petiole color: Upper surface: 146A. Lower surface: Close to 146B.

Flower description:

*Flower type and habit.*—Small salverform flowers arranged in axillary umbels; flowers face mostly upward or outward. Flowers self-cleaning. Very freely flowering with potentially two inflorescences per node; typically about 32 flowers per umbel.

*Natural flowering season.*—Spring until frost in the autumn; flowering continuous and consistent.

*Flower longevity on the plant.*—About one week.

*Fragrance.*—Faint, spicy, pleasant.

*Inflorescence diameter.*—About 4.1 cm.

*Inflorescence height.*—About 1.8 cm.

*Flowers.*—Appearance: Flared trumpet, corolla fused, four-parted; flowers roughly rectangular in shape. Diameter: About 1 cm by 9 mm. Corolla tube length: About 1.3 cm.

*Flower buds* (*before showing color*).—Length: About 4 mm. Diameter: About 5 mm. Shape: Roughly spherical. Color: 144A.

*Corolla.*—Arrangement/appearance: Single whorl of four petals, fused into flared trumpet. Petal length from throat: Upper and lower petals: About 5 mm. Lateral petals: About 4.5 mm. Petal width: Upper and lower petals: About 7 mm. Lateral petals: About 4 mm. Petal shape: Spatulate to somewhat orbicular. Petal apex: Rounded with slight emargination. Petal margin: Entire. Petal texture: Smooth, velvety. Color: Petal, upper surface, when opening: White, close to 155D, overlain with 9A. Petal, lower surface, when opening: 9D. Petal, upper surface, fully opened: White, close to 155D, overlain with 61A. Petal, lower surface and tube, fully opened: White, close to 155D, underlain with 61A. Throat: 13A.

*Calyx.*—Arrangement/appearance: One single calyx tube per flower. Calyx length: About 1.8 mm. Calyx width: About 1.5 mm. Apex: Two-pointed. Texture: Pubescent. Color, both surfaces: 144C.

*Peduncles.*—Length: About 1.8 cm. Diameter: About 1 mm. Angle: About 45° from the stem. Strength: Flexible, but strong. Texture: Pubescent. Color: 144A.

*Pedicels.*—Length: Less than 1 mm. Diameter: Less than 1 mm. Angle: About 45° from the stem. Strength: Flexible, but strong. Texture: Pubescent. Color: Close to 144A.

*Reproductive organs.*—Stamens: Quantity/arrangement: Four per flower, adnate to floral tube. Filament length: About 7 mm. Filament color: Close to 155D. Anther shape: Ovoid. Anther length: Less than 1 mm. Anther color: 14A. Pollen amount: Scarce. Pollen color: 12A. Pistils: Quantity: One per flower. Pistil length: About 3 mm. Stigma shape: Globular. Stigma color: Close to 151C. Ovary color: Close to 144A.

*Fruit.*—Type: Drupe. Length: About 5 mm. Diameter: About 5 mm. Texture: Smooth. Color: Immature: 144A. Mature: Close to 187A.

*Seed.*—Quantity per fruit: Two. Size: About 2 mm by 2 mm. Color: Close to 150D.

Disease/pest resistance: Plants of the new Lantana grown in the garden have been noted to be resistant to pathogens or pests common to Lantana. When grown in the greenhouse, plants of the new Lantana have been observed to be attractive to whiteflies.

Weather tolerance: Plants of the new Lantana have been observed to be very tolerant to rain and wind.

Temperature tolerance: Plants of the new Lantana have been observed to be tolerant to temperatures ranging from 0 to 38° C.

It is claimed:

1. A new and distinct cultivar of Lantana plant named 'Robpatpas', as illustrated and described.

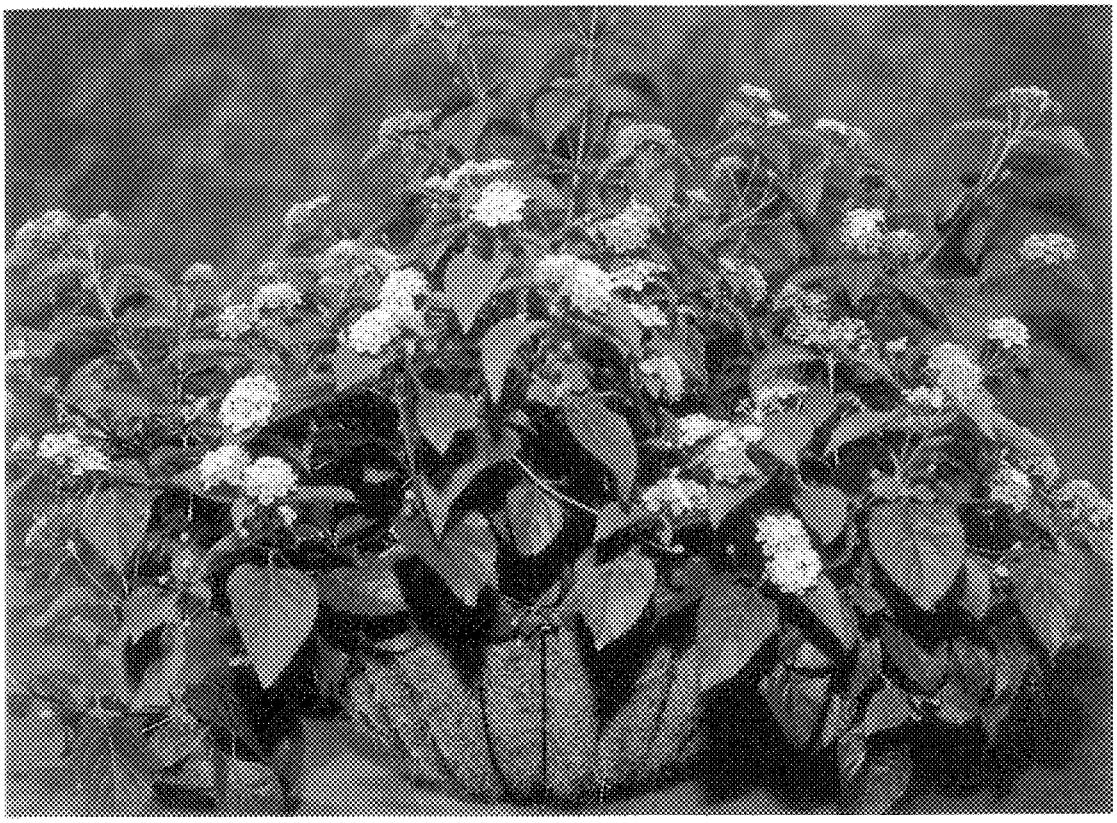

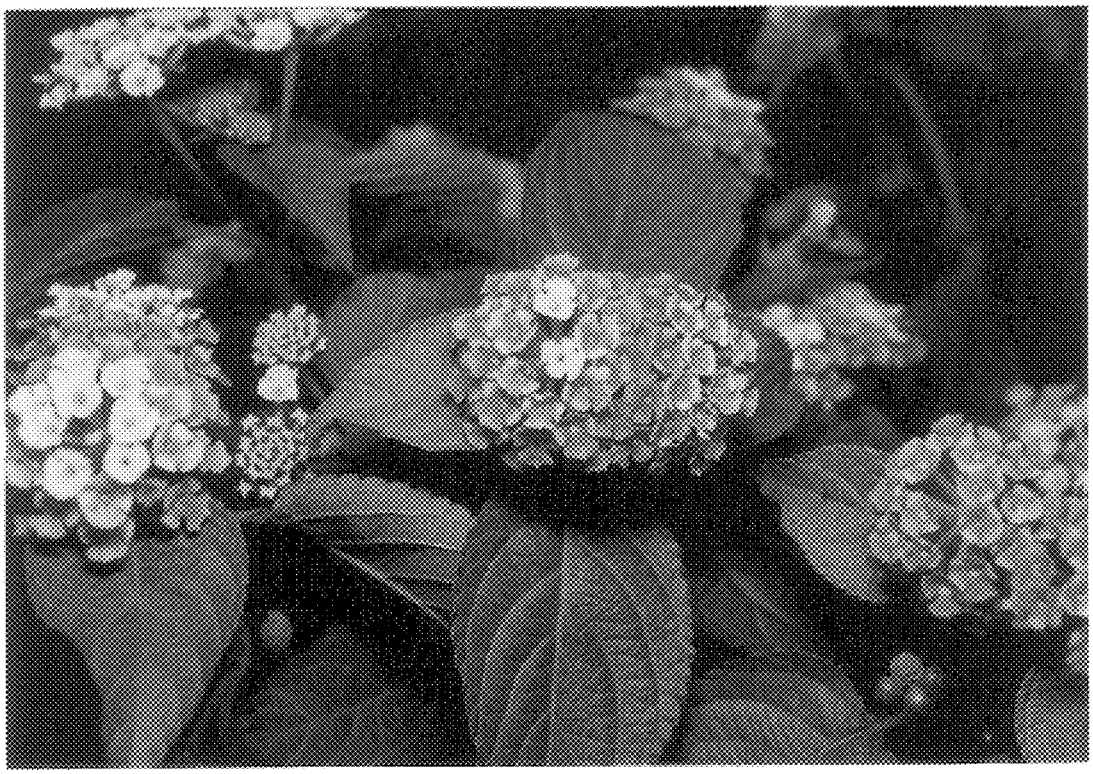

* * * * *